United States Patent [19]
Riza

[11] Patent Number: 5,817,111
[45] Date of Patent: Oct. 6, 1998

[54] OPEN LOOP SUTURE SNARE

[76] Inventor: Erol D. Riza, 550 Riverside Dr., Rossford, Ohio 43460

[21] Appl. No.: 858,220

[22] Filed: Mar. 28, 1997

Related U.S. Application Data

[60] Provisional application No. 60/014,360 Mar. 28, 1996.
[51] Int. Cl.⁶ ...................................................... A61B 17/00
[52] U.S. Cl. ............................ 606/148; 606/139; 112/169
[58] Field of Search ................................ 606/1, 110, 113, 606/126, 133, 139, 144, 148, 151, 187, 222–227; 112/80.03, 169

[56] References Cited

U.S. PATENT DOCUMENTS

| | | |
|---|---|---|
| 1,708,578 | 4/1929 | Hyde . |
| 3,630,190 | 12/1971 | Baker . |
| 3,877,434 | 4/1975 | Ferguson et al. . |
| 4,002,169 | 1/1977 | Cupler, II . |
| 4,230,123 | 10/1980 | Hawkins, Jr. . |
| 4,378,019 | 3/1983 | Yamada . |
| 4,616,656 | 10/1986 | Nicholson et al. . |
| 4,641,652 | 2/1987 | Hutterer et al. . |
| 4,779,616 | 10/1988 | Johnson . |
| 4,796,626 | 1/1989 | DeVries . |
| 4,935,008 | 6/1990 | Lewis, Jr. . |
| 5,106,369 | 4/1992 | Christmas . |
| 5,172,701 | 12/1992 | Leigh . |
| 5,217,024 | 6/1993 | Dorsey et al. . |
| 5,242,456 | 9/1993 | Nash et al. ............................... 606/142 |
| 5,250,054 | 10/1993 | Li ............................................ 606/148 |
| 5,261,917 | 11/1993 | Hasson et al. ........................... 606/139 |
| 5,281,237 | 1/1994 | Gimpelson ............................... 606/144 |
| 5,364,410 | 11/1994 | Failla et al. .............................. 606/148 |
| 5,387,227 | 2/1995 | Grice ...................................... 606/222 |
| 5,405,354 | 4/1995 | Sarrett .................................... 606/148 |
| 5,501,692 | 3/1996 | Riza ....................................... 606/148 |
| 5,573,542 | 11/1996 | Stevens ................................... 606/144 |
| 5,618,290 | 4/1997 | Toy et al. ................................ 606/139 |
| 5,653,716 | 8/1997 | Malo et al. .............................. 606/139 |
| 5,658,299 | 8/1997 | Hart ....................................... 606/139 |

FOREIGN PATENT DOCUMENTS 969254  10/1992  U.S.S.R. .

OTHER PUBLICATIONS

Product Brochure for RANFAC® Pneumoperitoneum Insufflation Needle (undated).
Catalog page for Suture Retriever, Copyright 1988 Acufex Microsurgical, Inc.
"Endoscopic Technique for ACL Reconstruction With Pro-Trac® Tibial Guide", Copyright 1991 Acufex Microsurgical, Inc.

Primary Examiner—Michael Buiz
Assistant Examiner—David O. Reip
Attorney, Agent, or Firm—MacMillan, Sobanski & Todd, LLC

[57] ABSTRACT

A surgical instrument for facilitating the use of sutures in arthroscopic, laparoscopic or other similar surgical procedures includes a housing having an internal cavity. A plunger extends within the cavity of the housing and is supported therein for relative sliding movement between first and second axial positions. A spring disposed within the cavity urges the plunger to the first axial position. A tubular introducer needle is secured to the housing and extends co-axially therefrom. An extension tube is disposed within the introducer needle and is secured to the plunger for axial movement therewith relative to the housing. The extension tube has an extension finger axially extending therefrom. A resilient wire having a wire finger portion is operatively coupled to the extension tube. When the plunger is in the first position, the extension finger and the wire finger are retracted within the introducer needle so that the wire extends generally alongside the extension finger in a closed position. When the plunger is in the second position, the extension finger and the wire finger are extended outwardly from the introducer needle. The wire is resiliently predisposed to urge said wire finger radially outwardly from the extension finger to an open position.

16 Claims, 9 Drawing Sheets

OPEN LOOP SUTURE SNARE

CROSS REFERENCE TO RELATED APPLICATIONS

This application claims the benefit of U.S. Provisional Application No. 60/014,360 filed Mar. 28, 1996.

BACKGROUND OF THE INVENTION

This invention relates in general to surgical instruments and in particular to a surgical snare instrument for facilitating the use of sutures in arthroscopic, laparoscopic or other similar surgical procedures.

Laparoscopic and arthroscopic surgeries are less invasive than conventional surgery and, therefore, may be performed using only a local anesthetic. Such surgeries typically involve puncturing the body tissue, such as the abdominal wall in laparoscopic surgery. A hollow cylindrical tube, known as a cannula, is inserted into the puncture and is subsequently used as a conduit through which one or more elongated surgical instruments may be inserted into the body opening. If desired, a plurality of punctures may be formed through the body tissue to facilitate the use of several surgical instruments.

During surgeries, the blood vessels in the punctured body tissue may be injured and cause significant bleeding during the puncturing. When this occurs, it is necessary to stop such bleeding. Cauterization and the use of a folley-ballon tamponade technique have been used in the past for stopping these body wall bleeders during surgery. Although effective, these techniques are somewhat cumbersome and may result in undesirable delays or, at times, abandonment of the surgical procedure. Sutures are well known for stopping external bleeding and are relatively quick and simple to employ. However, sutures are not usually employed in laparoscopic surgery because of difficulties in introducing and using them in the abdominal wall. Thus it would be desirable to provide for an improved surgical instrument for facilitating the use of sutures in surgical procedures.

BRIEF SUMMARY OF THE INVENTION

This invention relates in general to a surgical suture snare instrument for facilitating the use of sutures in arthroscopic, laparoscopic or other similar surgical procedures. The suture snare instrument includes a generally hollow housing which is formed having pair of circumferential flanges formed thereabout. The housing is formed having an internal cylindrical cavity which defines an internal diameter and extends from an opened end to a closed end. A plunger having an enlarged head extends within the cavity of the housing and is supported therein for relative sliding movement between first and second axial positions. A coiled spring disposed within the cavity urges the plunger to the first axial position. A tubular introducer needle is secured to the housing and extends co-axially therefrom. An extension tube is disposed within the introducer needle and is secured to the plunger for axial movement therewith relative to the housing. The extension tube has an extension finger axially extending therefrom. Preferably, the extension finger has a blunt tipped end portion to decrease the chance of mistakenly puncturing tissue. A resilient wire having a wire finger portion is operatively coupled to the extension tube. Preferably, the wire finger has a curved end to assist in snaring a suture. When the plunger is in the first position, the extension finger and the wire finger are retracted within the introducer needle so that the wire extends generally alongside the extension finger in a closed position. When the plunger is in the second position, the extension finger and the wire finger are extended outwardly from the introducer needle. The wire is resiliently predisposed to urge said wire finger radially outwardly from the extension finger to an open position.

Various objects and advantages of this invention will become apparent to those skilled in the art from the following detailed description of the preferred embodiment, when read in light of the accompanying drawings.

DETAILED DESCRIPTION OF THE INVENTION

Figure 1:
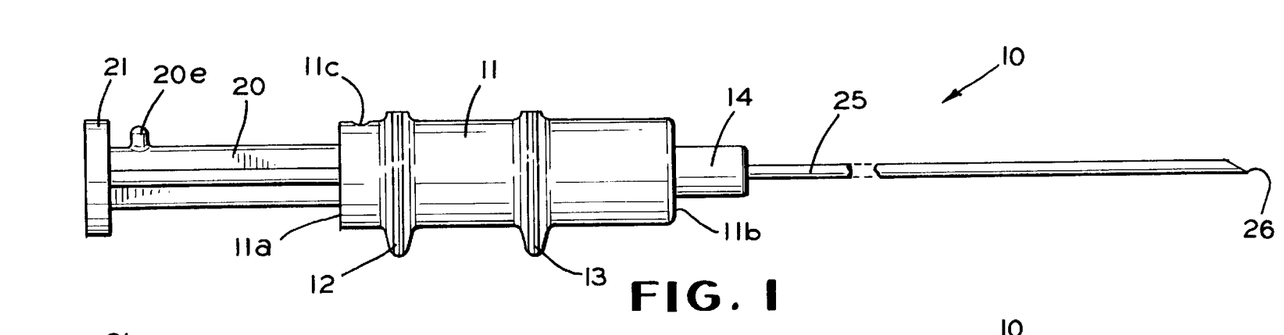
FIG. 1 is a side elevational view of a first embodiment of a suture snare instrument in accordance with this invention, wherein the plunger of the suture snare instrument is shown in the first axial position relative to the housing.
Figure 2:
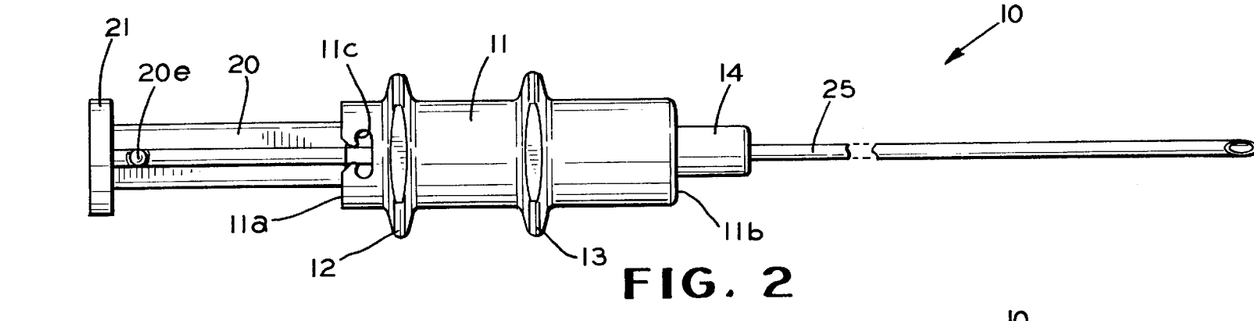
FIG. 2 is a top plan view of the suture snare instrument illustrated in FIG. 1.

Referring now to the drawings, there is illustrated in FIGS. 1 through 9 a first embodiment of a suture snare instrument, indicated generally at 10, in accordance to this invention. The suture snare instrument 10 includes a generally hollow cylindrical housing 11 having a proximal end 11a and a distal end 11b. The housing 11 includes first and second circumferential flanges 12 and 13 formed thereabout. The first circumferential flange 12 is located adjacent to the proximal end 11a of the housing 11, while the second circumferential flange 13 is located adjacent to the distal end 11b of the housing 11. Thus, the flanges 12 and 13 are axially spaced apart from one another, preferably by a distance of about three-fourths of one inch. The flanges 12 and 13 function as grips for grasping the housing 11. The housing 11 preferably includes a co-axial extension 14 provided at the distal end 11b thereof. The extension 14 is smaller in diameter than the housing 11 and is preferably formed integrally therewith. The housing 11 preferably is formed with a T-shaped slot 11c, as best shown in FIG. 2, formed through the upper portion of the housing 11 at the proximal end 11a thereof. The reason for the T-shaped slot 11c will be discussed below. Preferably, the entire housing 11 is formed from a molded plastic material but can be made of any suitable material.

Figure 5:
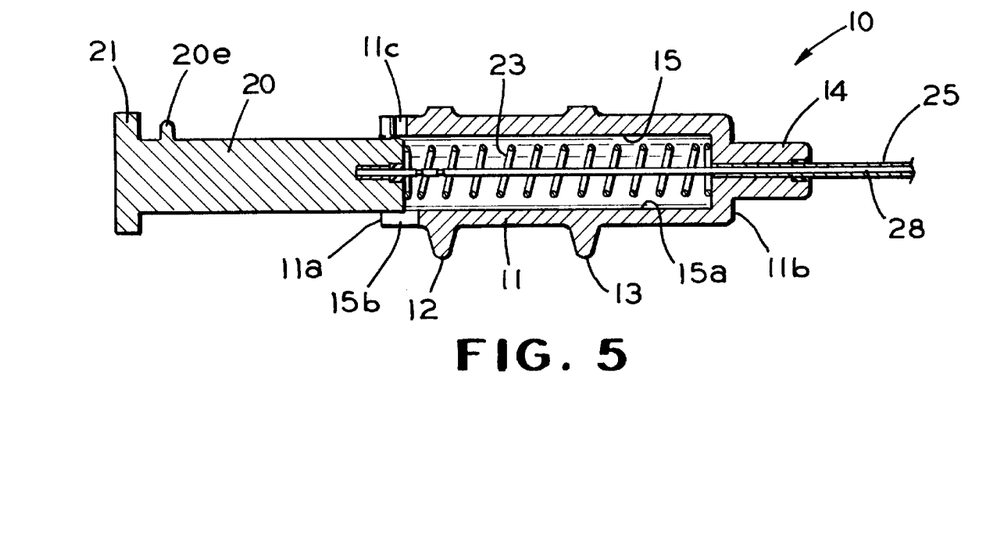
FIG. 5 is a sectional view of the suture snare instrument illustrated in FIG. 1.
Figures 6, 7:
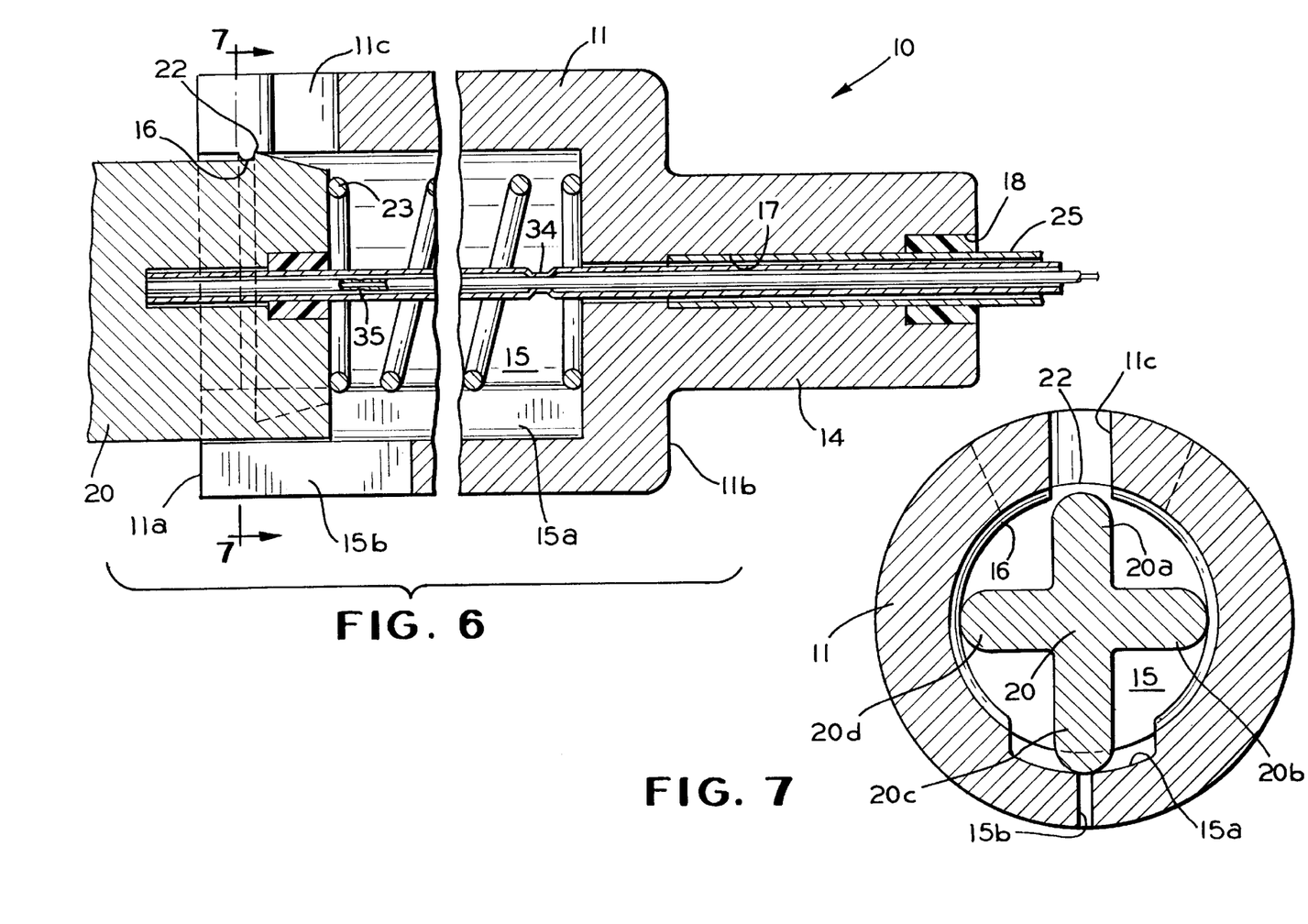
FIG. 6 is an enlarged fragmentary sectional view of the first and second ends of the housing of the suture snare instrument illustrated in FIG. 1.
FIG. 7 is a cross-sectional view of the suture snare instrument taken along lines 7—7 of FIG. 6.

Referring now to FIGS. 5 through 7, the internal structure of the housing 11 is illustrated in detail. As shown therein, the housing 11 is formed having an internal cylindrical cavity 15. The cavity 15 defines an internal diameter and extends from an opened end at the proximal end 11a of the housing 11 to a closed end adjacent the distal end 11b of the housing 11. An axially outwardly extending recess 15a is formed in the lower portion of the inner surface of the housing 11. The recess 15a extends from the open end of the proximal end 11a of the housing 11 throughout most or all of the cavity 15. As best shown in FIG. 7, the axially extending sides of the recess 15a define an arc relative to the longitudinal axis of the housing 11. The purpose of the recess 15a will be discussed below. An axially extending slot 15b is formed through the lower portion of the housing 11 at the proximal end 11a thereof. The purpose of the slot 15b will be discussed below. A small radially inwardly extending ridge 16 is formed about the circumference of the opening defined at the proximal end 11a of the housing 11 by the cavity 15. The purpose of this ridge 16 will be explained below. A co-axial passageway 17 extends from the cavity 15 through the extension 14 to a co-axial recess 18 formed in the distal end 11b of the housing 11. The purpose of the passageway 17 and the recess 18 will be explained below.

The suture snare instrument 10 also includes a plunger 20 having an enlarged head 21 formed at one end. The plunger 20 extends within the cavity 15 of the housing 11. As best shown in FIG. 7, the plunger 20 is formed generally in the shape of a cross having four radially outwardly extending web portions 20a, 20b, 20c, and 20d. The ends of the web portions 20a, 20b, 20c, and 20d abut the inner surface of the cavity 15 of the housing 11 to support the plunger 20 therein for axial sliding movement. The web portion 20c extends radially outwardly slightly further than the remaining web portions 20a, 20b, and 20d. As a result, the web portion 20c extends into the recess 15a formed in the housing 11. The cooperation of the web portion 20c with the recess 15a limits the ability of the plunger 20 to rotate relative to the housing 11 to the arc defined by the longitudinal sides of the recess 15a, the reason form which will be explained below. As best shown in FIGS. 6 and 7, a small radially outwardly extending ridge 22 is partially circumferentially formed about the end of the plunger 20 opposite the head 21. The plunger 20 has a radially extending pin 20e formed thereon which can selectively engage the T-shaped slot 11c formed on the housing 11. The purpose of the ridge 22 and the slot 11c will be explained below. As with the housing 11, the entire plunger 20 is preferably formed from a molded plastic material.

Figure 3:
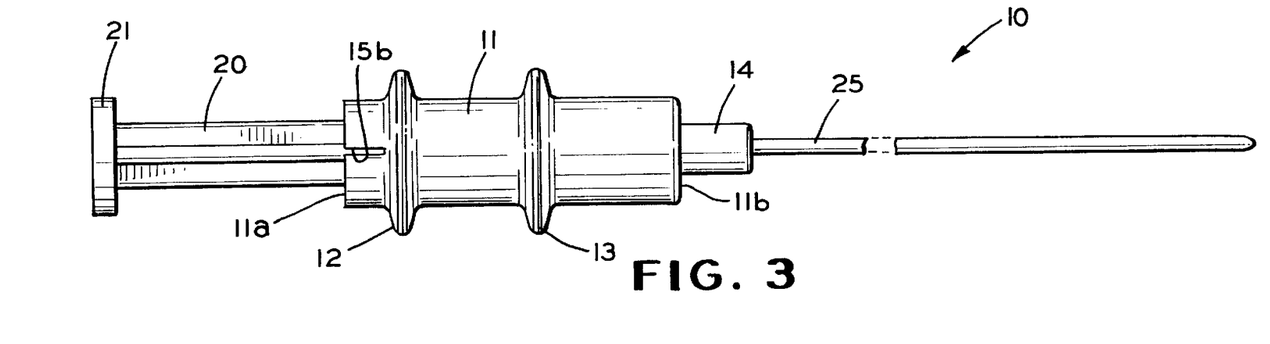
FIG. 3 is a bottom plan view of the suture snare instrument illustrated in FIG. 1.
Figure 4:
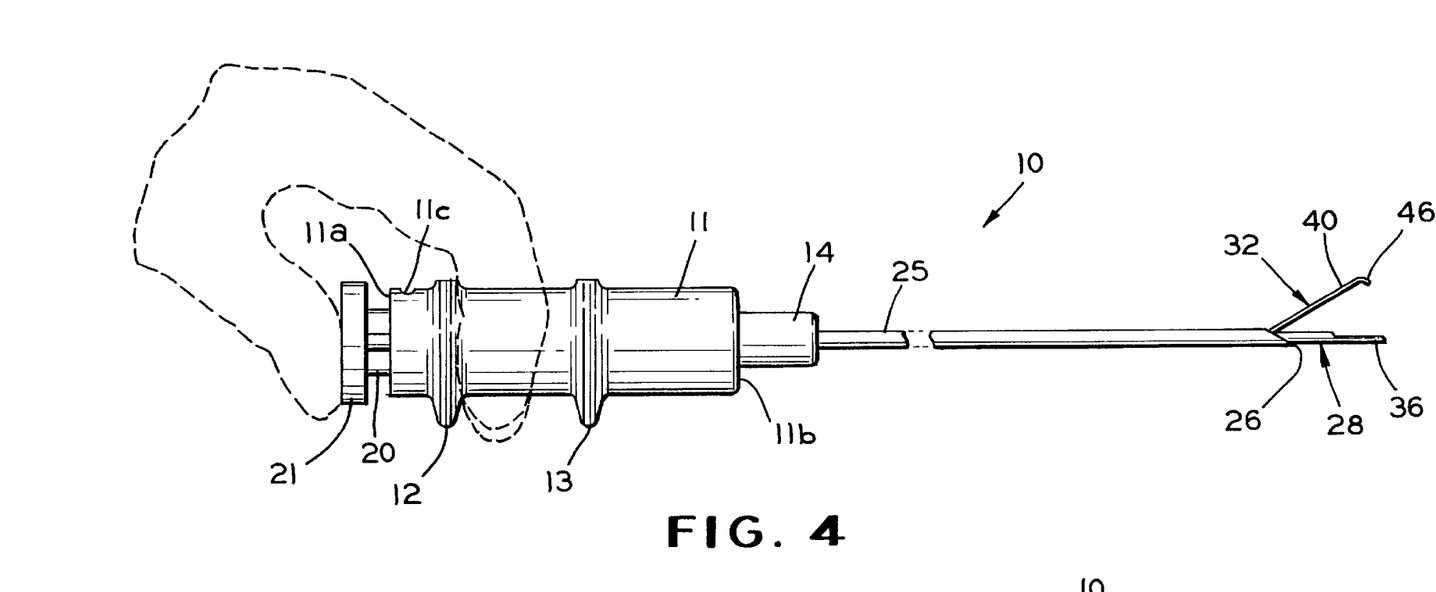
FIG. 4 is a side elevational view similar to FIG. 1, wherein the plunger of the suture snare instrument is shown in the second axial position relative to the housing.

A coiled spring 23 or any other suitable resilient structure is disposed within the cavity 15. The ends of the spring 23 react against the inner end of the plunger 20 (adjacent to the ridge 22) and the end wall of the closed end of the cavity 15. Thus, the spring 23 urges the plunger 20 to a first axial position relative to the housing 11, as shown in FIGS. 1, 3, and 4. When in this position, the inner ridge 16 formed on the housing 11 engages the outer ridge 22 formed on the plunger 20. As a result, the plunger 20 is not ejected from the housing 11 under the urging of the spring 23. The slot 15b formed through the lower portion of the housing 11 allows the adjacent portions of the housing 11 to resiliently deflect radially outwardly during assembly of the suture snare instrument 10 when the plunger 20 is inserted into the cavity 15 of the housing 11. The plunger 20 may be moved to a second axial position within the housing 11 against the urging of the spring 23 by applying an appropriate force thereto. Typically, this force will be applied by squeezing with the fingers and thumb of a hand, such as shown in dotted lines in FIG. 4. The plunger 20 can be held in the second axial position by slightly rotating the plunger 20 relative to the housing 11 to cause the pin 20c to selectively engage the T-shaped slot 11c. Note that the web portion 20c of the plunger 20 can rotate about a limited arcuate range within the recess 15a to allow the pin 20c to be positioned within the T-shaped slot 11c.

The suture snare instrument 10 further includes a tubular metallic introducer needle 25. The introducer needle 25 is secured to the axial extension 14 of the housing 11 and extends co-axially therefrom. Referring to FIG. 6, a proximal end of the introducer needle 25 extends through the recess 18 into a press fit relationship within the passageway 17 of the extension 14. Preferably the recess 18 is then filled with an adhesive material to secure the introducer needle 25 to the housing 11. However, the first end of the introducer needle 25 may be fixed to the housing 11 by any suitable means, such as by integrally molding the housing 11 about the needle 25 or by a mechanical fastener. The distal end of the introducer needle 25 is preferably provided with a sharp point 26. The housing 11, the plunger 20, the spring 23, and the introducer needle 25 are similar in construction as those of the suture snare instrument's described in my U.S. Pat. No. 5,501,692 which is hereby incorporated by reference.

The suture snare instrument 10 further includes an elongated extension tube 28 which is disposed within the introducer needle 25. A proximal end of the extension tube 28 is secured to the inner end of the plunger 20 by any suitable means, such as those described above for securing the first end of the introducer needle 25 to the housing 11. Thus, the extension tube 28 is secured to the plunger 20 for axial movement therewith relative to the housing 11. The extension tube 28 extends through the cavity 15, the passageway 17, and into the introducer needle 25.

The suture snare instrument 10 further includes an inner tube 30 which is disposed within the extension tube 28. A flexible resilient metallic wire 32 is disposed within the inner tube 30. In the illustrated embodiment, the extension tube 28 is crimped about the inner tube 30 at a location 34 to effect the connection therebetween. Also, the inner tube 30 is crimped about the wire 32 at a location 35 to effect the connection therebetween. As a result, the extension tube 28, the inner tube 30, and the wire 32 are jointly connected together for movement through the introducer needle 25 when the plunger 20 is moved as described above. Of course, the wire 32, the inner tube 30, and the extension tube 28 can be jointly connected by multiple crimps or by any other suitable means. If desired, the suture snare instrument 10 can be used without the inner tube 30, in which the extension tube 28 is directly crimped to the wire 32.

Figures 8, 9, 10:
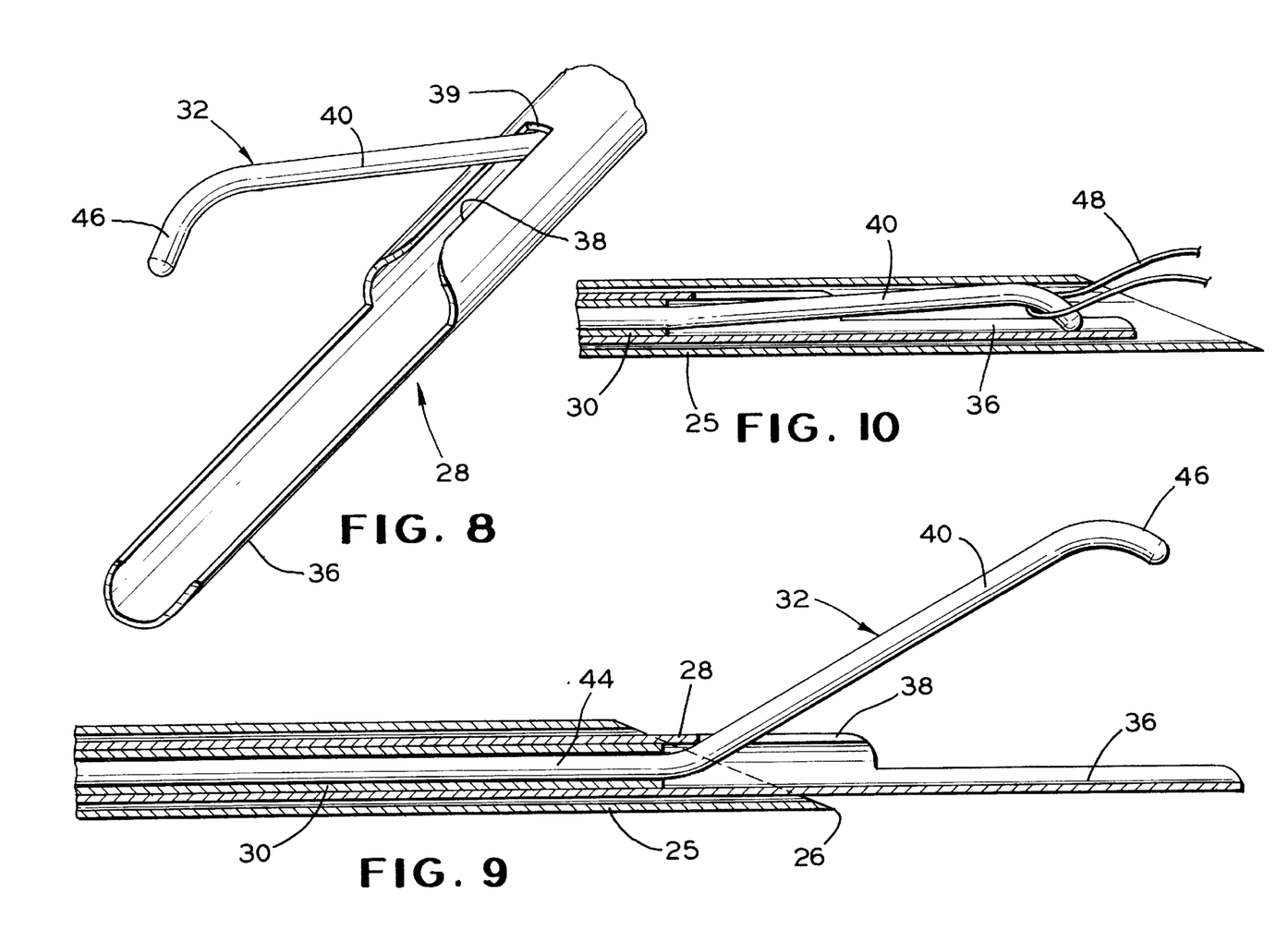
FIG. 8 is a perspective view of the end of the extension tube of the suture snare instrument illustrating the wire finger extended outwardly from the extension tube finger of the extension tube.
FIG. 9 is an enlarged partial sectional view of the tip of the suture snare instrument illustrated in FIG. 4.
FIG. 10 is a view similar to FIG. 9 except showing the wire finger thereof in a closed position.

When the plunger 20 is moved to the second axial position, as described above, the distal end of the extension tube 28 extends beyond the sharp point 26 of the introducer needle 25 as shown in FIG. 9. The distal end of the extension tube 28 has a finger 36 which axially extends from the extension tube 28. As illustrated in FIG. 8, the extension tube finger 36 can be formed by removing a longitudinally extending portion of the end of the extension tube 28, thereby forming the extension tube finger 36 into a semi-tubular channel shape, as best shown in FIG. 8. The distal end of the extension tube 28 also has an axial slot 38 extending from the extension tube finger 36 a short distance toward the housing 11. The slot 38 has a width which is slightly larger than the diameter of the wire 32, the purpose of which will be explained below.

The distal end of the wire 32 has a permanently deformed finger portion 40 which angularly extends from a main portion 44 of the wire 32. The wire finger 40 ends in a permanently deformed wire end 46 which is resiliently predisposed to assume an arcuate shape. The tip of the wire end 46 is preferably rounded to avoid inadvertent puncture. The wire 32 is preferably comprised of a shape memory alloy, such as Nickel-Titanium alloy (NiTi), for superior shape holding properties.

When the extension tube 28, inner tube 30, and the wire 32 have been fixed to the plunger 20 during manufacture, they are passed from the cavity 15, through the passageway 17, and into the introducer needle 25. To aid in assembly, a restraining tube (not shown) can be temporarily inserted over the collapsed wire finger 40 and the extension tube finger 36 prior to insertion in the passageway 17. The restraining tube is sized so as to fit inside the introducer needle 25, and is removed after assembly of the suture snare instrument 10.

When the plunger 20 is in the first axial position, as illustrated in FIG. 10, the extension tube 28, the inner tube 30 and the wire 32 are located in a retracted position within the introducer needle 25. As a result the wire finger 40 and the extension tube finger 36 are withdrawn within the introducer needle 25. The wire finger 40 will be resiliently deflected so as to assume the general shape of the surrounding introducer needle 25.

When the plunger 20 is moved to the second axial position, as illustrated in FIGS. 4, 8, and 9, the extension tube 28, the inner tube 30, and the wire 32 are moved to an extended position relative to the introducer needle 25. As a result, the wire finger 40 is extended outward from the extension tube finger 36, and extends radially outwardly through the slot 38, the purpose of which will be discussed below.

It will normally be desirable to be able to have the wire finger 40 be held in an extended position outwardly from the extension tube finger 36 without the surgeon having to continuously apply pressure with his or her thumb to the plunger 20. Therefore, the suture snare instrument 10 is preferably provided with cooperating locking features, such as the pin 20e and the T-shaped slot 11c as described above.

The suture snare instrument 10 is preferably utilized to insert and tie sutures in a laparoscopic surgical procedure. To accomplished this, the housing 11 is supported by the index and middle fingers of one hand (shown in dotted lines in FIG. 4) extending between the flanges 12 and 13. The thumb of the same hand is used to selectively depress the plunger 20 for movement between the first and second axial positions relative to the housing 11. When the plunger 20 is depressed, the wire finger 40 and the extension tube finger 36 are extended from the end of the introducer needle 25. Simultaneously, the wire finger 40 resiliently flexes outwardly from the extension tube finger 36 to an open position shown in FIG. 6. When so extended, a suture 48, shown in FIG. 10 can be positioned between the wire finger 40 and the extension tube finger 36. Then, the plunger 20 is released so that the spring 23 urges the plunger 20 to return to the first axial position. As a result, the wire finger 40 is retracted within the introducer needle 25 causing the wire finger 40 to flatten toward the extension tube finger 36 to the closed position shown in FIG. 10. As illustrated therein, the curved wire end 46 cooperates with the extension tube finger 36 to form a closed loop which entraps the suture 48. The suture 48 is retracted within the introducer needle 25 with the wire finger 40 and the extension tube finger 36. Thus, the suture 48 is frictionally captured by the suture snare instrument 10.

The suture snare instrument 10 may be manipulated such that the sharp angled end 26 of the introducer needle 25 is passed through a selected portion of body tissue (not shown), together with the end of the suture 48 engaged thereby. Next, the plunger 20 is moved to the second axial position, which again extends the wire finger 40 and the extension tube finger 36 outwardly from the end of the introducer needle 25. Again, the wire finger 40 extends outwardly from the extension tube finger 36 to the open position, releasing the frictional engagement of the end of the suture 48. The suture snare instrument 10 can be then manipulated to drop the end of the suture 48. Then, plunger 20 can be released to retract the wire finger 40 and extension finger 36 back within the introducer needle 25, and the introducer needle 25 can be withdrawn from the body tissue, leaving the end of the suture 48 inside the body tissue. The suture snare instrument 10 is then manipulated such that the introducer needle 25 is inserted into another selected portion of body tissue. The plunger 20 is then moved to the second axial position, and the end of the suture 48 is captured by the cooperation of the wire finger 40 and the extension tube finger 36 as described above. The plunger 20 is released to the first axial position and the suture 48 is withdrawn into the introducer needle 25 and is frictionally held between the closed extension tube finger 36 and the wire finger 40. The suture snare instrument 10 is withdrawn from the body tissue, and the suture 48 is released. The suture 48 can then be tied in any conventional manner.

Figures 11, 12, 13, 14:
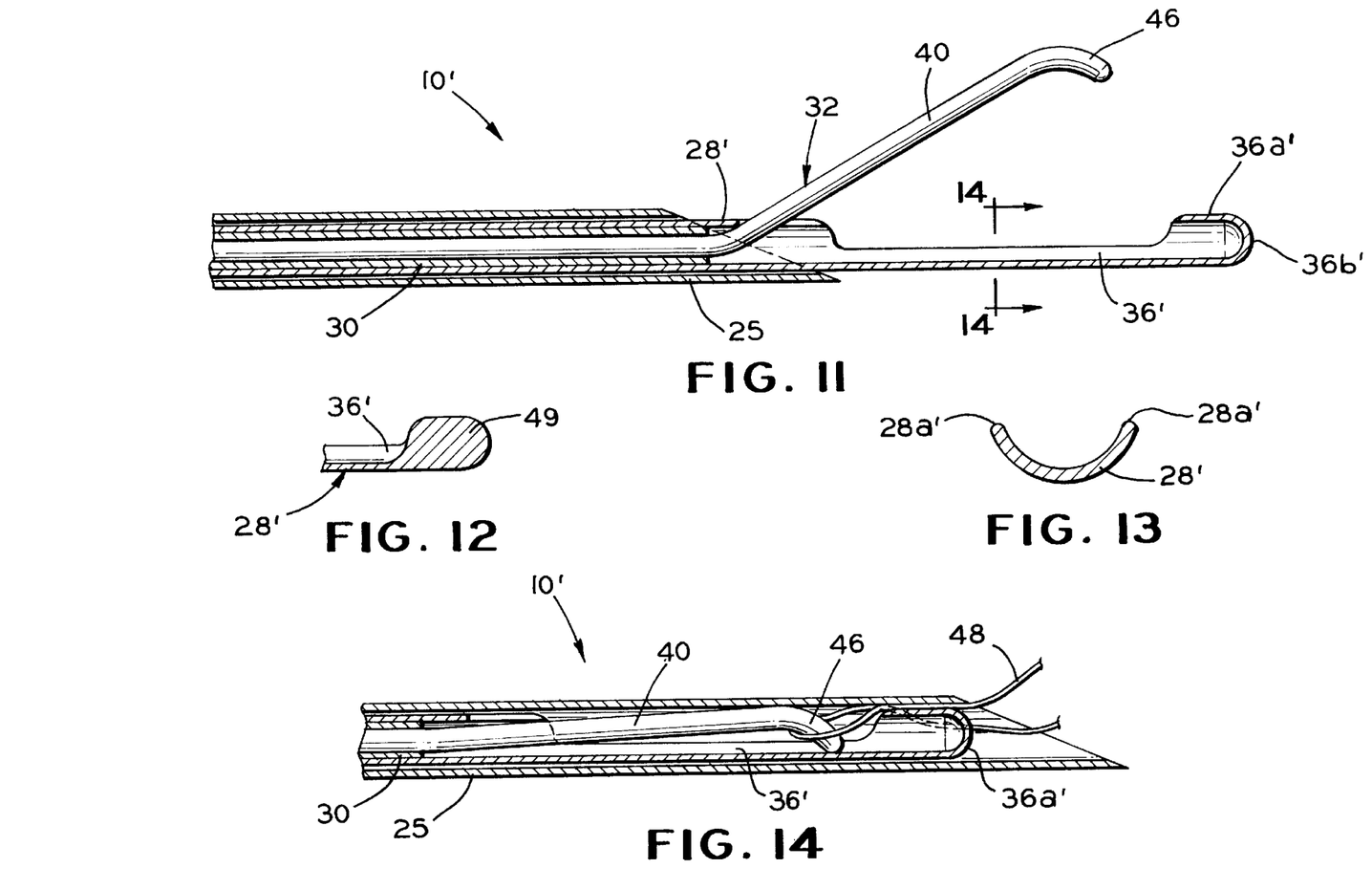
FIG. 11 is an enlarged partial sectional view of the tip of a second embodiment of a suture snare instrument.
FIG. 12 is a partial sectional view of the end of the extension tube shown in FIG. 11, illustrating an alternate arrangement for closing the end of the extension tube.
FIG. 13 is a view similar to FIG. 11 illustrating the fingers thereof in a closed position.
FIG. 14 is cross-sectional view taken along lines 14—14 of FIG. 11 showing the rounded edges of the extension tube.

FIG. 11 is an enlarged partial sectional view of the tip of a second embodiment of a suture snare instrument 10' which is similar to the suture snare instrument 10 shown in FIG. 9. Like structures are labeled with the same associated reference numbers. The suture snare instrument 10' includes an extension tube 28' having a extension tube finger 36'. The extension tube finger 36' has an end portion 36a' having a blunt rounded tip 36b'. The end portion 36a' can be formed hollow, as shown in FIG. 6B, or can be formed as a solid structure, such as the end portion 49 shown in FIG. 6C. The rounded tip 36b' of the end portion 36a' decreases the chance of mistakenly puncturing tissue and causing injury during use of the suture snare instrument 10'. As can be seen from FIG. 13, which is a partial sectional view of the retracted suture snare instrument 10', the diameter of the end portion 36a' is slightly smaller than the inside diameter of the introducer needle 25. Thus, the end portion 36a' provides for a tight annular clearance for the suture 48 which slightly compresses two portions of the suture between the end portion 36a' and the inside wall of the introducer needle 25. This tight clearance provides for a slight frictional engagement with the suture 48 to help prevent inadvertent drawing of the suture 48 through the loop created by the wire end 46 and the extension tube finger 36' when in the closed position.

Another difference between the suture snare instrument 10 and the suture snare instrument 10' is that the extension tube 28' has a slot 38' which is shorter in length than the slot 38 of the suture snare instrument 10. The shorter slot 38' helps prevent suture entanglement in the mechanism of the suture snare instrument 10' as the extension tube 28' retracts. As seen in FIG. 14 which is a cross-section of the extension tube 28', the extension tube 28' has exposed edges 28a' which are preferably rounded over to prevent cutting of the suture by the wire finger 40 and slot 38'. The edges of the extension tube 28' adjacent the slot 38' are likewise preferably rounded over to avoid cutting the suture.

Figure 15:
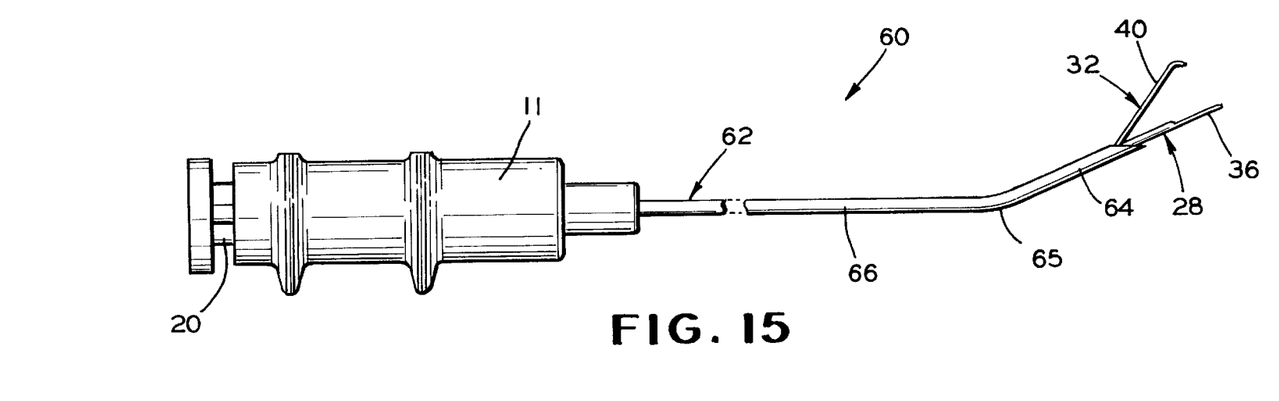
FIG. 15 is a side elevational view of a third embodiment of a suture snare instrument in accordance with this invention, wherein the end of the introducer needle is angled with respect to a main portion of the introducer needle.

FIG. 15 illustrates a third embodiment of the invention similar to the suture snare instrument 10 of FIG. 1 in which like reference numbers will indicate similar parts. The suture snare instrument 60 includes an introducer needle 62 having an angled end 64. The suture snare instrument 60 is shown with the plunger 20 thereof in the second axial position. In the illustrated condition, the wire finger 40 of the wire 32 and the extension tube finger 36 of the extension tube 28 extend outwardly from the introducer needle 62 in an open position arrangement. The end 64 of the introducer needle 62 is angled at a relatively permanent bend 65. The bend 65 can be formed with the end 64 held at any suitable angle relative to a main portion 66 of the introducer needle 62. The bend 65 is desirable under certain circumstances in which the introducer needle 62 is manipulated around various body members, such as ligaments and muscle tissue during an arthroscopic surgical procedure. The bend 65 also helps visualization of the end 64 during laparoscopic surgery.

Preferably, both the extension tube 28 and the wire 32 are comprised of a shape memory alloy for superior shape holding properties. The shape memory alloy is particularly suited for structures which are disposed within the introducer needle 62 and are moved through the bend 65 when the plunger 20 is moved from the first axial position to the second axial position and vice versa.

Figure 16:
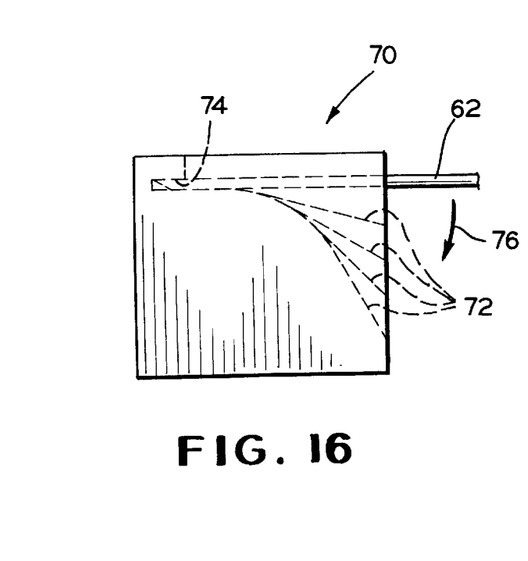
FIG. 16 is a side elevational view of a tube bending fixture to provide a means for angling the end of the introducer needle illustrated in FIG. 15.
Figure 17:
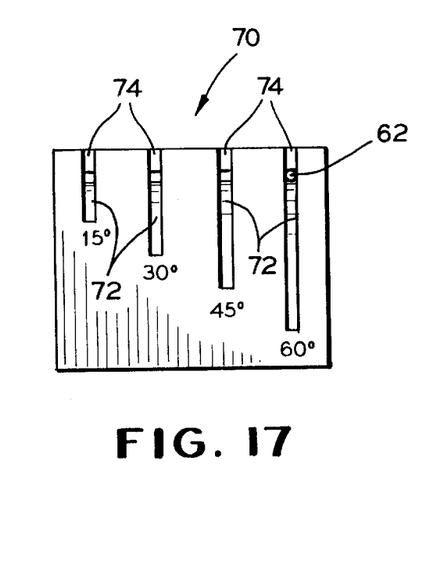
FIG. 17 is a front elevational view of the tube bending fixture illustrated in FIG. 16.
Figure 18:
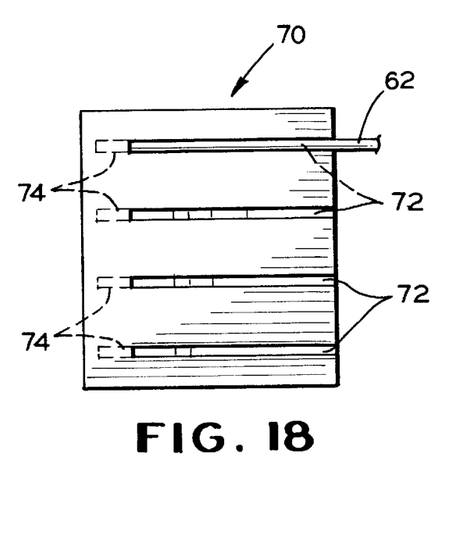
FIG. 18 is a top plan view of the tube bending fixture illustrated in FIG. 16.

To provide for the bend 65 on the introducer needle 62, a tube bending fixture 70, shown in FIGS. 16 through 18, may be used. The tube bending fixture 70 preferably has a plurality of grooves 72, each having a unique curvature, as can be seen from FIG. 16. A straight introducer needle 62 is inserted into a recess 74, which is located at one end of each groove 72 and supports the distal end of the introducer needle 62. The introducer needle 62 is then forced in a direction indicated by an arrow 76 (downward, as shown in FIG. 16) until the introducer needle 62 is in contact with the full length of the groove 72, so that the introducer needle 62 is bent at the same angle as the corresponding groove 72. An introducer needle 62 having an already formed bend 65 can be bent at an increased angle by inserting the introducer needle 62 into the tube bending fixture 70 and repeating the procedure described above to form the increased bend 65.

Figures 19, 20:
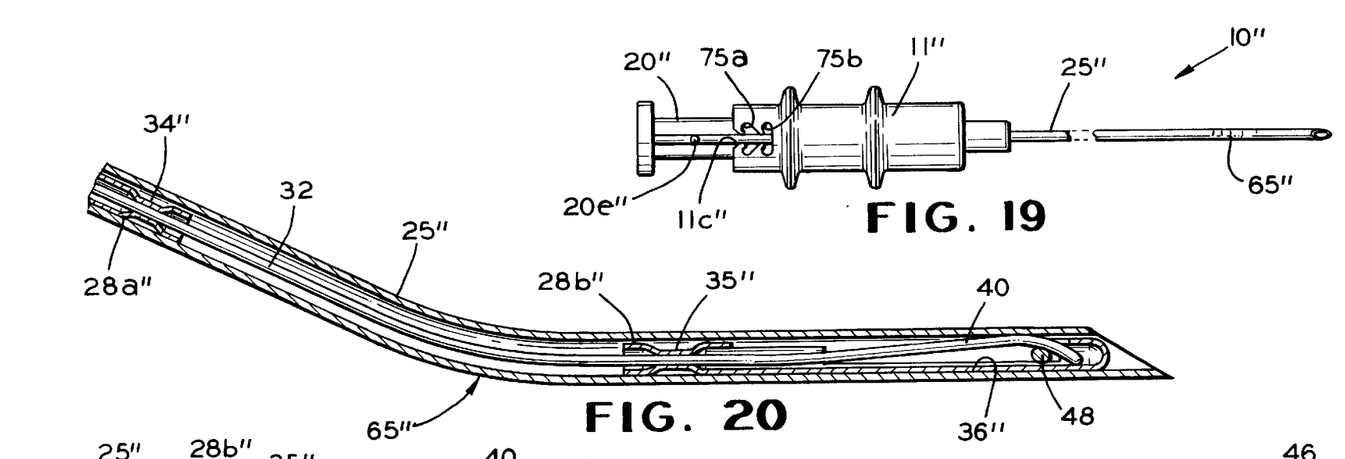
FIG. 19 is a top plan view of a fourth embodiment of a suture snare instrument.
FIG. 20 is an enlarged partial sectional view of the tip of the suture snare instrument of FIG. 19, wherein the wire finger and extension tube finger are in a retracted position.

FIG. 19 is a top plan view of a fourth embodiment of a suture snare instrument 10" which is similar to the suture snare instruments 10, 10', and 60. As before, like reference numbers will indicate similar parts.

A first difference between the suture snare instrument 10" and the suture snare instruments 10, 10' and 60 is in the shape of a slot 11c" formed in the upper portion of a housing 11" of the suture snare instrument 10". The slot 11c" has a pair of axially spaced apart branches 75a and 75b for receiving a radially extending pin 20e" formed on a plunger 20". Preferably, the slot 11c" also includes a second pair of branches forming a lateral mirror image of the branches 75a and 75b. The slot 11c" and the pin 20e" provide for positioning of the plunger 20" at multiple axial locations, the reason for which will be explained below. It will be appreciated that the housing 11" of the suture snare instrument 10" can be formed without a slot 11c", or a slot having any suitable number of branches.

Another difference between the suture snare instrument 10" and the suture snare instrument 10 is that the introducer needle 25" of the suture snare instrument 10" has a bend 65" at the distal end thereof.

Another difference between the suture snare instrument 10" and the suture snare instruments 10, 10', and 60 is the absence of an inner tube similar to the inner tube 30 in the suture snare instrument 10. As shown in FIG. 20, the suture snare instrument 10" has first and second extension tubes 28a" and 28b" disposed within the introducer needle 25". The first and second extension tubes 28a" and 28b" are axially spaced apart form one another in the region of the bend 65". The proximal end of the first extension tube 28a" is preferably fastened to the plunger 20" in the same manner that the extension tube 28 is fastened to the plunger 20", as described above with respect to FIG. 6. The first extension tube 28a" is crimped to the wire 32 at a location 34" to effect a fixed connection therebetween. The second extension tube 28b" includes an extension tube finger 36" similar to the extension tube finger 36' of FIG. 11. The second extension tube 28b" is crimped to the wire 32 at a location 35" to effect a fixed connection therebetween. Because of the axial spacing of the first and second extension tubes 28a" and 28b" at the bend 65" of the introducer needle 25", only the wire 32 is flexed through the bend 65" as the plunger 20" is operated. This arrangement produces less resistance to operation of the plunger 20" to operate the wire finger 40 and the extension tube finger 36" of the suture snare instrument 10" than if the tubes 28a" and 28b" were replaced by a single extension tube similar to the extension tubes 36 and 36'. The first and second extension tubes 28a" and 28b" can also be made of a material having relatively low flexibility, compared to the extension tubes 36 and 36', since the extension tubes 28a" and 28b" are not forced through the bend 65".

Figures 21, 22, 23:
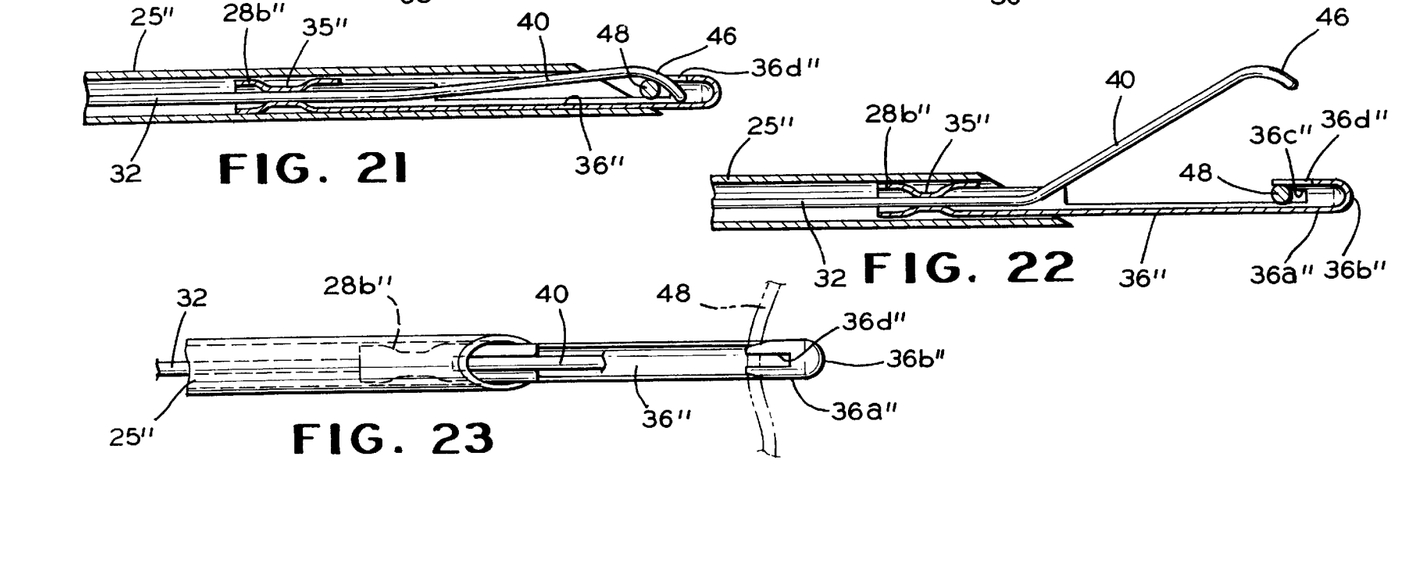
FIG. 21 is an enlarged partial sectional view of the tip of the suture snare instrument of FIG. 19, wherein the wire finger and extension tube finger are in an intermediate position.
FIG. 22 is an enlarged partial sectional view of the tip of the suture snare instrument of FIG. 19, wherein the wire finger and extension tube finger are in an extended position.
FIG. 23 is an enlarged top plan elevational view of the tip of the suture snare instrument of FIG. 22.

As best shown in FIGS. 22 and 23, the second extension tube finger 36" has a hook shaped end portion 36a" having a blunt rounded tip 36b". The tip 36b" can be formed hollow or solid, similar to the tip 36b'. The tubular wall of the end portion 36a" has a pair of lateral opposed slots 36c" formed so that the upper portion of the end portion 36a" (as viewed in FIG. 22) generally forms a proximally opening hook. A longitudinally extending slot 36d" is vertically formed in the upper portion of the tubular wall of the end portion 36a" (as viewed in FIG. 22). Thus, the tip 36b" can be seen to form a pair of proximally opening, transversely spaced apart hooks in the upper portion of the end portion 36a". As will be further explained below, the slot 36d" between these hooks has a width which is slightly larger than the diameter of the wire 32 to permit passage of the wire end 46 therethrough.

The plunger 20" of the suture snare instrument 10" can be moved and retained in generally three axial positions: a first axial position, an intermediate axial position, and a second axial position. In the first axial position, the plunger 20 is in the position shown in FIG. 19, and the wire finger 40 and the second extension tube finger 36" are in a retracted position within the introducer needle 25", as shown in FIG. 20. In the retracted position, the wire finger 40 and the second extension tube finger 36" cooperate to frictionally capture the suture 48 between the inner wall of the introducer needle 25" and the end portion 36a" of the second extension tube finger 36". In the intermediate axial position, the pin 20e" of the plunger 20" is axially adjacent the branch 75a of the slot 11c". The plunger 20" can be rotated about the longitudinal axis thereof to permit the pin 20e" to be captured in the branch 75a.

In the intermediate axial position, the wire finger 40 and the second extension tube finger 36" are partially extended from the distal end of the introducer needle 25", as shown in FIG. 21. In this position, the wire end 46 is positioned within the slot 36d" between the hooks of the tip 36b". Thus it can be seen that the wire finger 40 and the second extension tube finger 36" cooperate to form a closed loop to encircle the suture 48. Although the suture 48 is encircled by the wire finger 40 and the second extension tube finger 36", the suture 48 is not frictionally captured therebetween, thereby permitting movement of the wire finger 40 and the second extension tube finger 36" along the length of the suture 48. Thus the suture snare instrument 10" can be repositioned with respect to the suture 48.

In the second axial position, the plunger 20" is fully depressed into the housing 11", and the pin 20e" is axially aligned with the branch 75b of the slot 11c". If desired, the plunger 20"e can be rotated about the longitudinal axis thereof so that pin 20e" is captured in the branch 75b of the slot 11c". In this condition, the plunger may be released and the plunger will remain in the second axial position. In the second axial position, as shown in FIG. 22, the wire finger 40 and the second extension tube finger 36" are extended fully from the introducer needle 25". The wire finger 40 and the second extension tube finger 36" cooperate to form an open loop. The open loop thus formed may be used to capture, manipulate, and release objects such as the suture 48 without having to thread the suture 48 therethrough, as is the case in a closed loop suture snare. The hook shaped end portion 36a" of the extension tube finger 36" aids is especially useful in snaring and retaining the suture 48 while the plunger 20" is moved from the second position to the intermediate or first positions.

FIGS. 24 through 27 illustrate the tip of a fifth embodiment of a suture snare instrument, indicated generally at 77. The suture snare instrument 77 has a pair of cooperating wire fingers 78 and 79, instead of having a single wire finger 40 and one extension tube finger 36 as the previously described suture snare instruments 10, 10', 10" and 60. The wire fingers 78 and 79 are shown in a retracted position in FIG. 24, and are in an extended position in FIG. 25. An extension tube 80 is fastened to the plunger (not shown) and is slidably disposed within the introducer needle 25. The wire fingers 78 and 79 are preferably comprised of a shape memory alloy, and have tail portions 78a and 79a, respectively. The wire fingers 78 and 79 further include rounded end portions 78b and 79b, respectively.

Figures 24, 25, 26, 27:
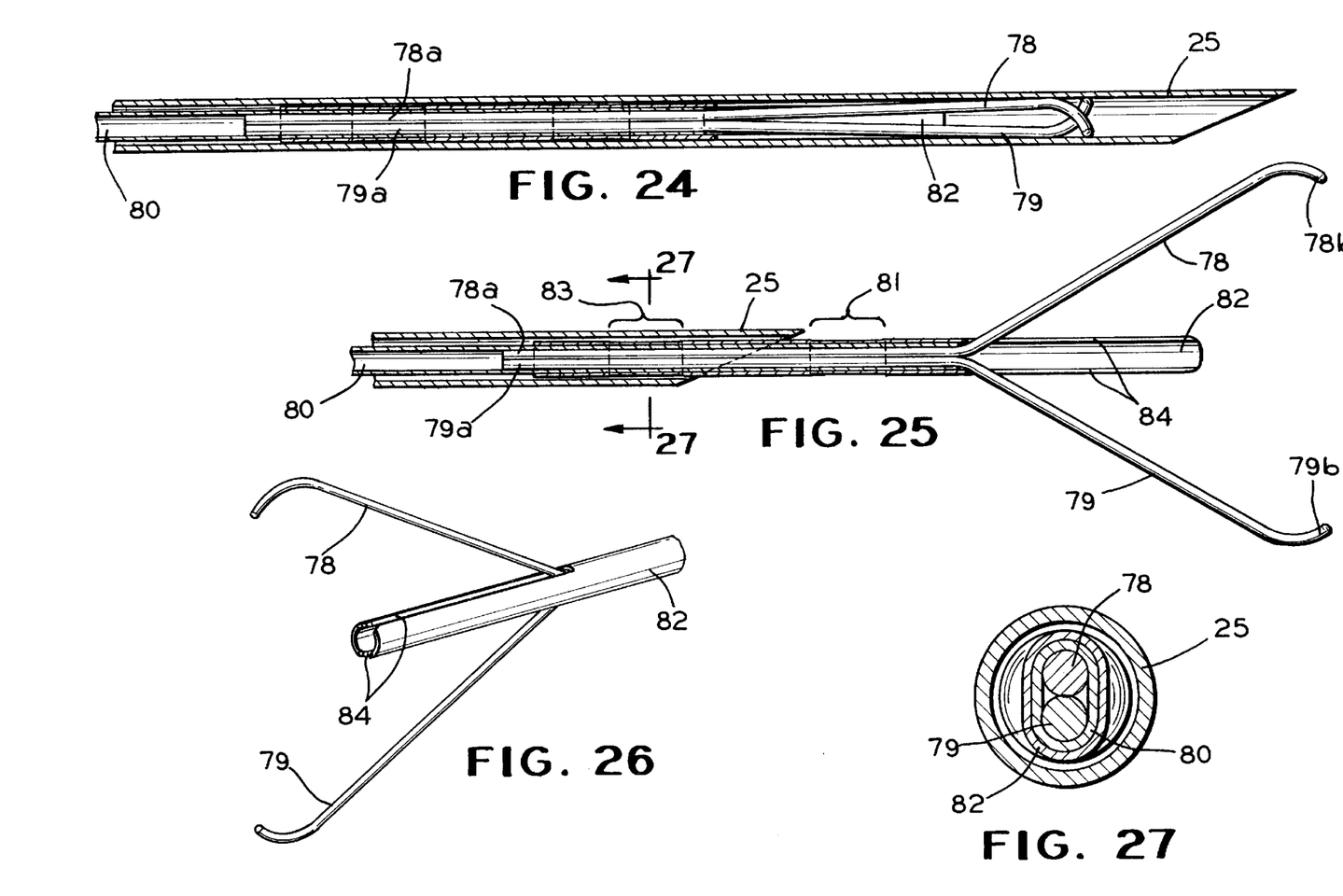
FIG. 24 is an enlarged side sectional view of the tip of a suture snare instrument illustrating a fifth embodiment of the suture snare instrument in accordance with this invention, having a pair of cooperating wire fingers, wherein the wire fingers are in a retracted position.
FIG. 25 is a view similar to FIG. 24 except showing the pair of wire fingers in an extended position.
FIG. 26 is a perspective view of the end of the extension tube of FIG. 25, showing the pair of wire fingers in the extended position.
FIG. 27 is a view taken along lines 27—27 of FIG. 25.

The extension tube 80 is crimped about the wire finger tail portions 78a and 79a at a location 81 to effect the connection between the wire fingers 78 and the extension tube 80. The end of the extension tube 80 is disposed within a guide tube 82. The guide tube 82 is crimped about the extension tube 80 at a location 83 so that the guide tube 82 is frictionally engaged with the extension tube 80. As a result, the guide tube 82, the extension tube 80, and the wire fingers 78 and 79 are frictionally engaged jointly with each other so that when the plunger 20 is moved to the second axial position, the wire fingers 78 and 79 and the guide tube 82 are extended outwardly from the introducer needle 25. When the plunger 20 is in the second axial position, the wire fingers 78 and 79 resiliently move away from one another to an open position.

As best seen in FIG. 26, the wire fingers 78 and 79 extend outwardly through two opposed longitudinal slots 84 formed through the guide tube 82. The slots 84 guide the wire fingers 78 and 79 so that the wire fingers 78 and 79 are extended in opposing directions, and do not twist with respect to each other. The two wire fingers 78 and 79 cooperate with each other to manipulate a suture 48 in a manner similar to the manipulation of a suture 48 by the wire finger 40 and extension tube finger 36 of the suture snare instrument 10 shown in FIG. 1.

There is illustrated in FIG. 28 through 35 a sixth embodiment of a suture snare instrument of the present invention, indicated generally at 100. The suture snare instrument 100 includes a plunger 102, the details of which can be seen in FIGS. 30 and 31. The plunger 102 has a circular ring member 104, which is sized to accept a surgeons thumb. The plunger 102 also includes an extension 106 which extends outwardly from the ring member 104. The extension 106 has a rectangular slot 108 and a circular through hole 110. The proximal end of the hole 110 communicates with the slot 108, and the distal end of the hole 100 communicates with an end surface 112 of the extension 106.

Figures 28, 29, 30, 31, 32, 33, 34, 35:
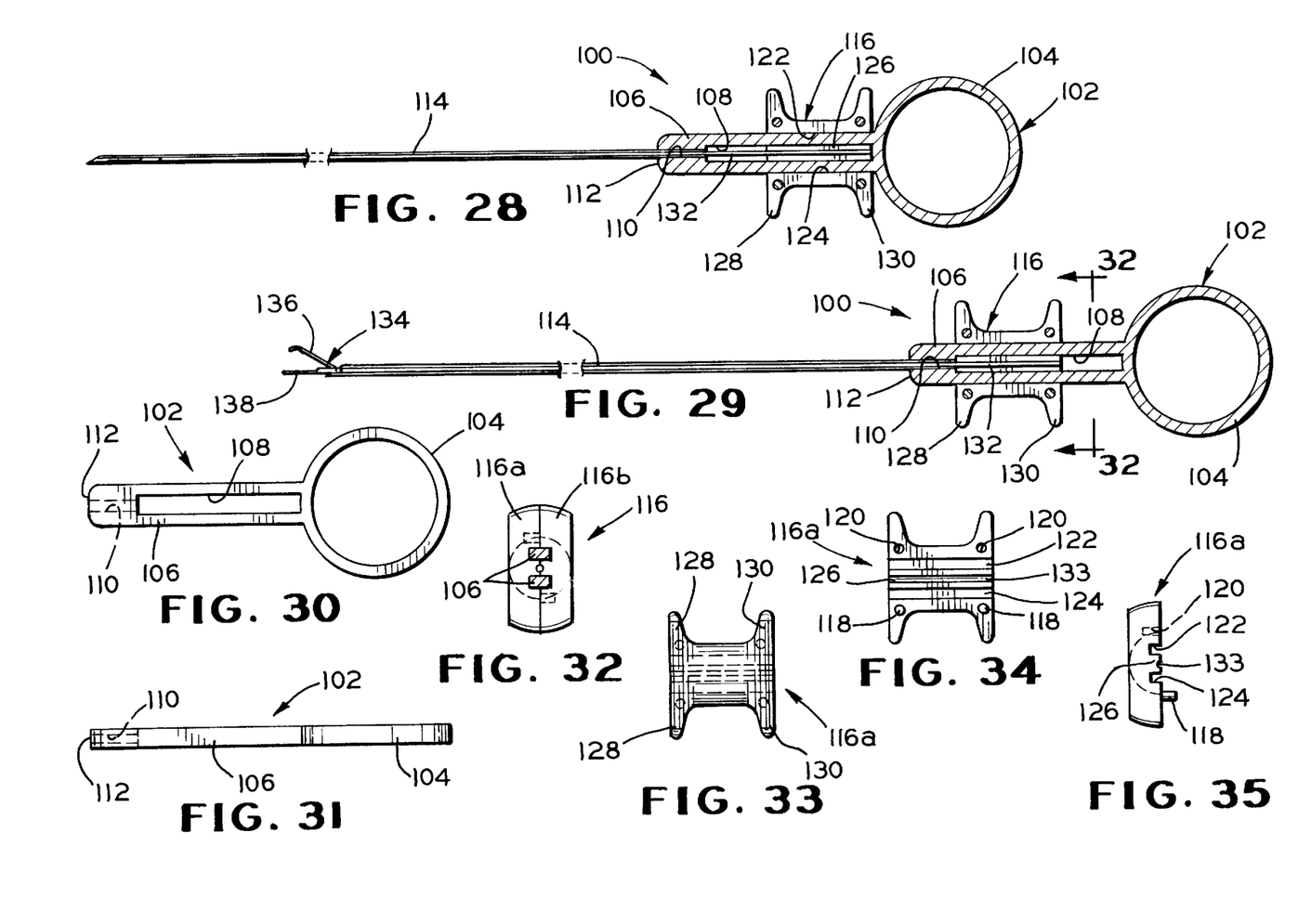
FIG. 28 is a side sectional view of a sixth embodiment of a suture snare instrument in accordance with this invention, wherein the body of the suture snare instrument is shown in a first axial position relative to the plunger, and the wire finger and the extension tube finger are in a retracted position within the introducer needle.
FIG. 29 is a view similar to FIG. 28 except showing the body of the suture snare instrument in a second axial position relative to the plunger with the wire finger and the extension tube finger are in an extended position with respect to the introducer needle.
FIG. 30 is a side elevational view of the plunger of the suture snare instrument illustrated in FIG. 28.
FIG. 31 is a top plan view of the plunger illustrated in FIG. 30.
FIG. 32 is a view of the suture snare instrument taken along lines 32—32 of FIG. 29, illustrating the plunger being slidably disposed within the body so that the central portion of the body is positioned within the slot of the plunger.
FIG. 33 is a side elevational view of a single body half of the suture snare instrument of FIG. 28, wherein two symmetrical body halves assembled together comprise the body.
FIG. 34 is a rear side elevational view of the body half illustrated in FIG. 33.
FIG. 35 is an end elevational view of the body half illustrated in FIG. 33, showing a connection pin and connection hole.

The suture snare instrument 100 further includes a hollow introducer needle 114. The introducer needle 114 is secured to the extension 106 of the plunger 102 by a press fit relationship between the proximal end of the introducer needle 114 and the inner wall of the hole 110 of the plunger 102. The introducer needle 114 can be attached to the plunger 102 by any other suitable means, such as those described above with respect to the introducer needle 25 and housing 11 of the suture snare instrument 10.

The suture snare instrument 100 further includes a body 116 which can be formed from two mating body halves 116a and 116b as shown in FIGS. 32 through 35. The two body halves 116a and 116b can be fastened together by adhesive bonding or by any other suitable means to form the body 116. The body halves 116a and 116b are aligned during assembly by a pair of connector pins 118 which are inserted into cooperating connector holes 120 in the adjoining body half 116a or 116b. The body 116 has two longitudinal slots 122 and 124 which extend throughout the length of the body 116. The slots 122 and 124 are separated by a central rib 126. The body 116 further includes a pair of transversely opposed flanges 128 and a pair of transversely opposed flanges 130, which pairs of flanges 128 and 130 are spaced apart from each other so as to function as finger grips.

The two halves 116a and 116b of the body 116 are assembled together such that the extension 106 of the plunger 102 is slidably disposed within the slots 122 and 124 of the body 116, and such that the central rib 126 of the body 116 is riding in the slot 108 of the plunger 102. The plunger 102 is, therefore, slidably mated with the body 116. The plunger 102 and the body 116 may be moved relative to one another along a longitudinal axis defined by the slot 108 of the plunger 102 and the slots 122 and 124 of the body 116. A spring (not shown) may be inserted into the slot 108 of the plunger 102 so as to bias the plunger 102 in a desired axial direction with respect to the body 116.

The suture snare instrument 100 further includes an elongated extension tube 132 which is slidably disposed within the introducer needle 114. The proximal end of the extension tube 132 is secured the central rib 126 of the body 116. The extension tube 132 can be secured to the body 116 by any suitable means. In the illustrated embodiment, each half of the rib 126 is provided with a longitudinal extending groove 133, as shown in FIGS. 34 and 35, so that the pair of mating grooves 133 form an axial bore through the rib 126, within which the extension tube 132 is adhesively fastened. A flexible metal wire 134, having a wire end 136, is attached to the extension tube 132. The extension tube 132 has a extension tube finger 138 at the free end thereof The extension tube 132 and wire 134 are similar in structure and function as the extension tube 28 and wire 32 of the suture snare instrument 10 shown in FIG. 1.

During operation of the suture snare instrument 100, the suture snare instrument 100 advantageously retracts the introducer needle 114 while leaving the extension tube 132 in place relative to a patient. This minimizes the possibility of accidental puncture since the wire end 136 remains at the same axial distance from the tissue of the patient. The wire end 136 opens radially, but does not move axially toward the patient out of the end of the introducer needle 114.

While the device of the invention is described as an open loop suture snare, it will be apparent to those of ordinary skill in the art that the device would also be useful as a grasper for manipulating a variety of items, including portions of body tissue and blood vessels.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A surgical instrument comprising:

a first tube having a first end, said first tube defining an axis;

a second tube slidably disposed within said first tube, said second tube having an extension, said extension having a semi-tublar channel shaped portion, said second tube being axially movable between a first position, wherein said extension is retracted within said first end of said first tube, and a second position, wherein said extension is axially extended outside of said first end of said first tube; and a resilient wire having a first end and a second end, said wire being fixed to said second tube at said second end such that, when said second tube is in said first position, said wire is in a closed position and extends generally alongside said extension of said second tube, said wire being extended outside of said first end of said first tube when said second tube is in said second position, said wire being resiliently predisposed to urge said first end of said wire radially outwardly from said extension of said second tube to an open position of said wire when said second tube is in said second position.

2. The surgical instrument of claim 1, wherein said first tube has a sharpened tip.

3. The surgical instrument of claim 1, wherein said first tube has a bend formed therein.

4. The surgical instrument of claim 1, wherein said first end of said wire is curved.

5. The surgical instrument of claim 1, wherein said first end of said wire has a blunt tip.

6. The surgical instrument of claim 1, wherein said second tube has a first slot formed therein adjacent said extension, said wire extending through said first slot when said wire is in said open position.

7. The surgical instrument of claim 1, wherein said second tube has an end portion positioned axially outwardly from said first end of said wire when said second tube is in said second position.

8. The surgical instrument of claim 7, wherein said end portion has a blunt rounded tip.

9. The surgical instrument of claim 7, wherein said end portion has an axially extending second slot, said first end of said wire extending through said slot of said end portion when said wire is in said open position.

10. The surgical instrument of claim 7, wherein said end portion has a third slot formed laterally through said end portion.

11. The surgical instrument of claim 1 further comprising:

a hollow housing defining an internal cavity, said first tube being connected to said housing; and a plunger slidably disposed within said internal cavity of said housing for relative movement between first and second axial positions, said second tube and said second end of said wire being connected to said plunger, wherein positioning of said plunger in said first axial position locates said extension in said first position and, said positioning of said plunger in said second axial position locates said extension in said second position.

12. The surgical instrument of claim 11 further comprising a spring disposed within said internal cavity urging said plunger toward said first position.

13. The surgical instrument of claim 11 further including means for locking said plunger in said second axial position.

14. The surgical instrument of claim 11 further in including means for limiting relative rotation between said plunger and said housing.

15. The surgical instrument of claim 1 further including a second resilient wire having a first end and a second end, said second wire being fixed to said second tube at said second end such that, when said second tube is in said first position, said second wire is in a closed position and extends generally alongside said extension of said second tube, said second wire being extended outside of said first end of said first tube when said second tube is in said second position, said second wire being resiliently predisposed to urge said first end of said second wire radially outwardly from said extension of said second tube to an open position of said second wire when said second tube is in said second position.

16. The surgical instrument of claim 1 further comprising:

a body having at least one slot formed therethrough, said second tube being connected to said body;

and a plunger slidably disposed within said at least one slot of said body for relative movement between first and second axial positions, said first tube being connected to said plunger, wherein positioning of said plunger in said first axial position locates said extension in said first position, and positioning of said plunger in said second axial position locates said extension in said second position.

\* \* \* \* \*